(12) United States Patent
Orbay et al.

(10) Patent No.: US 8,814,918 B2
(45) Date of Patent: Aug. 26, 2014

(54) FRACTURE FIXATION PLATE

(75) Inventors: Jorge L. Orbay, Miami, FL (US);
Thomas H. Norman, Miami, FL (US);
Juan Salcedo, Miami, FL (US)

(73) Assignee: Skeletal Dynamics, L.L.C., Miami, FL (US)

( * ) Notice: Subject to any disclaimer, the term of this patent is extended or adjusted under 35 U.S.C. 154(b) by 0 days.

(21) Appl. No.: 13/366,886

(22) Filed: Feb. 6, 2012

(65) Prior Publication Data

US 2012/0209333 A1   Aug. 16, 2012

Related U.S. Application Data

(60) Provisional application No. 61/442,595, filed on Feb. 14, 2011, provisional application No. 61/531,485, filed on Sep. 6, 2011, provisional application No. 61/536,316, filed on Sep. 19, 2011.

(51) Int. Cl.
*A61B 17/80* (2006.01)

(52) U.S. Cl.
USPC ............ 606/286; 606/280; 606/283; 606/284

(58) Field of Classification Search
USPC ....................... 606/286, 280, 70, 71, 283, 284
See application file for complete search history.

(56) References Cited

U.S. PATENT DOCUMENTS

| | | | |
|---|---|---|---|
| 6,283,969 B1 * | 9/2001 | Grusin et al. ................ | 606/280 |
| 6,358,250 B1 | 3/2002 | Orbay | |
| 6,364,882 B1 | 4/2002 | Orbay | |
| 6,440,135 B2 | 8/2002 | Orbay et al. | |
| 6,508,819 B1 | 1/2003 | Orbay | |
| 6,712,820 B2 | 3/2004 | Orbay | |
| 6,767,351 B2 | 7/2004 | Orbay et al. | |
| 6,866,665 B2 | 3/2005 | Orbay | |
| 6,893,444 B2 | 5/2005 | Orbay | |
| 7,250,053 B2 | 7/2007 | Orbay | |
| 7,282,053 B2 | 10/2007 | Orbay | |
| 7,294,130 B2 | 11/2007 | Orbay | |
| 7,335,204 B2 | 2/2008 | Tornier | |
| 7,527,639 B2 | 5/2009 | Orbay et al. | |
| 7,635,381 B2 | 12/2009 | Orbay | |
| 7,695,502 B2 | 4/2010 | Orbay et al. | |
| 7,780,711 B2 | 8/2010 | Orbay et al. | |
| 7,857,838 B2 | 12/2010 | Orbay | |
| 7,867,260 B2 | 1/2011 | Meyer et al. | |
| 7,905,909 B2 | 3/2011 | Orbay | |
| 2004/0210220 A1 | 10/2004 | Tornier | |
| 2006/0149250 A1 | 7/2006 | Castaneda et al. | |
| 2007/0123886 A1 | 5/2007 | Meyer et al. | |
| 2008/0119895 A1 | 5/2008 | Manceau | |
| 2009/0118769 A1 * | 5/2009 | Sixto et al. .................... | 606/280 |
| 2009/0143825 A1 | 6/2009 | Graham et al. | |
| 2010/0268283 A1 | 10/2010 | Orbay | |
| 2011/0166607 A1 | 7/2011 | Castaneda et al. | |
| 2011/0172669 A1 | 7/2011 | Castaneda et al. | |

* cited by examiner

*Primary Examiner* — Nicholas Woodall
*Assistant Examiner* — Christine Nelson
(74) *Attorney, Agent, or Firm* — Lott & Fischer, PL

(57) ABSTRACT

A plate for fracture fixation is provided including a plurality of individually adjustable heads and various features to achieve: a.) superior fixation of the plate to osteoporotic diaphyseal bone; b.) improved visualization of the fracture line; c.) intraoperative adjustability to achieve better contact of the plate and the bone; d.) reduced risk of post-surgery tendon rupture; d.) improved fixation of small volar marginal fragments and, e.) improved targeting and fixing of particular fractured bone fragments.

10 Claims, 13 Drawing Sheets

FRACTURE FIXATION PLATE

CLAIM OF PRIORITY

This application is being filed as a non-provisional patent application under 35 U.S.C. §111(b) and 37 CFR §1.53(c). This application claims priority under 35 U.S.C. §111(e) to U.S. provisional patent applications Ser. No. 61/442,595 filed on Feb. 14, 2011; Ser. No. 61/531,485 filed on Sep. 6, 2011 and Ser. No. 61/536,316 filed on Sep. 19, 2011, the contents of which are incorporated herein by reference.

FIELD OF INVENTION

The invention relates generally to the fixation of bone fractures and in particular to plates for the volar fixation of fractures of the distal radius.

BACKGROUND OF THE INVENTION

Fracture fixation plates for the distal radius are known in the art. In particular, volar fracture fixation plates for the treatment of the Colles' fracture are frequently used. While many existing plates are effective, in many instances they do not provide the means for: a.) good visualization of the fracture; b.) achieving good contact between the plate and the bone; c.) the need to target particular bone fragments; d.) the fixation of small volar marginal fragments and e.) accommodating for conditions such as morbidity of the patient in the form of osteoporotic diaphyseal bone. Furthermore, in a small but significant number of cases, known fracture fixation plates and/or the fasteners attached thereto can impinge upon flexor and/or extensor tendons, resulting in post-operative tendon injury or rupture.

SUMMARY OF THE INVENTION

It is among the objects of this invention to overcome the limitations of the heretofore-known devices by providing inventive features to achieve: a.) superior fixation of the plate to osteoporotic diaphyseal bone; b.) improved visualization of the fracture line; c.) intraoperative adjustability to achieve better contact of the plate and the bone; d.) reduction of the risk of post-surgery flexor and extensor tendon rupture; e.) improved fixation of small volar marginal fragments; and f.) improved targeting and fixation of particular fractured bone fragments.

Although the invention is illustrated and described herein as embodied in a volar fracture fixation plate for the distal radius it is nevertheless not intended to be limited to only the details shown, since various modifications and structural changes may be made therein without departing from the spirit of the invention and within the scope and range of equivalents of the claims.

The construction of the invention, however, together with additional objects and advantages thereof will be best understood from the following description of the specific disclosed embodiments when read in connection with the accompanying drawings.

For purpose of the descriptions of the invention that follow, "bottom" refers to the bone contacting surface of a plate and "top" refers to the opposite surface.

DETAILED DESCRIPTION OF THE INVENTION

Figure 1:
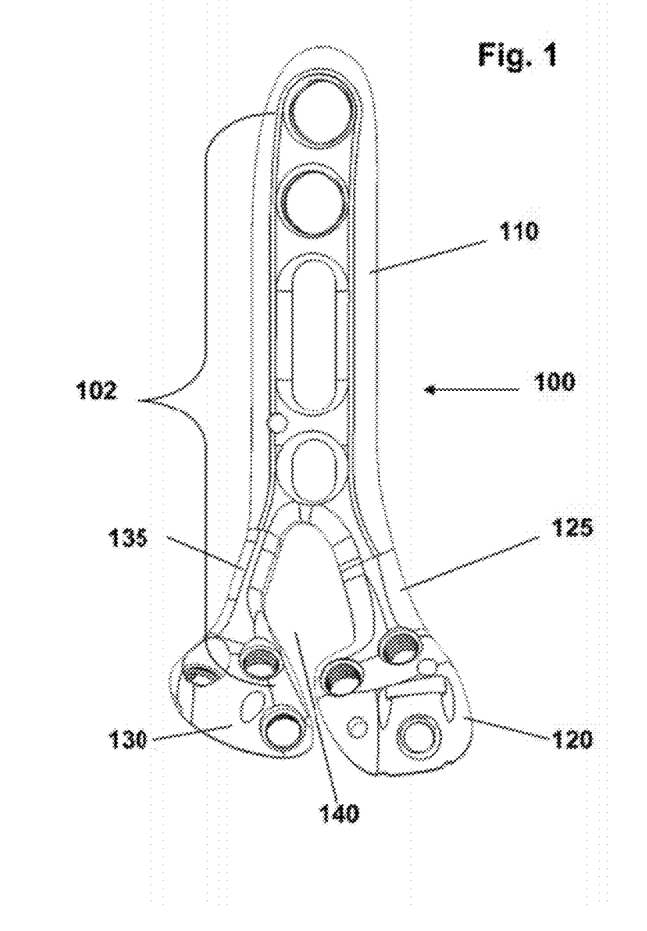
FIG. 1 is a top view of a fracture fixation plate in accordance with the present invention.
Figure 2:
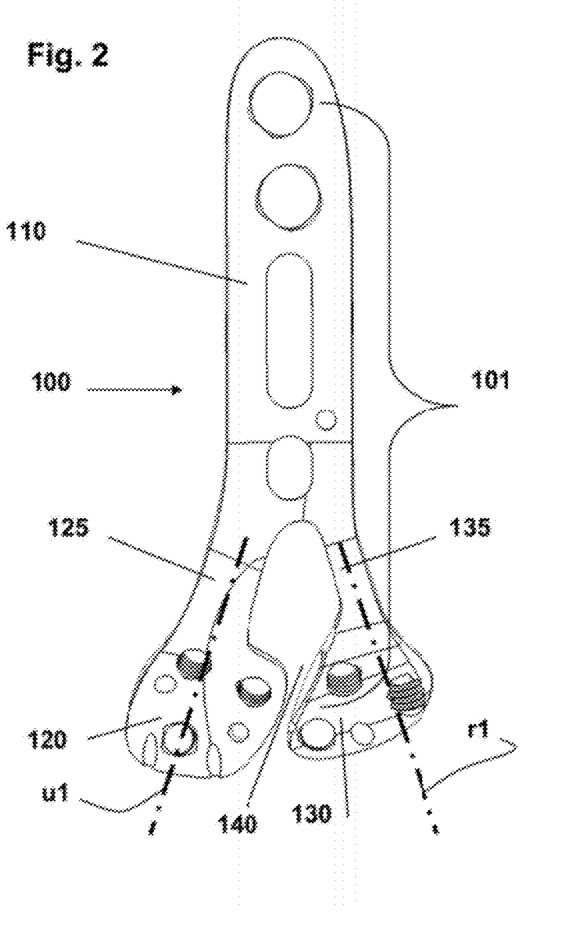
FIG. 2 is a bottom view of a fracture fixation plate in accordance with the present invention.
Figure 3:
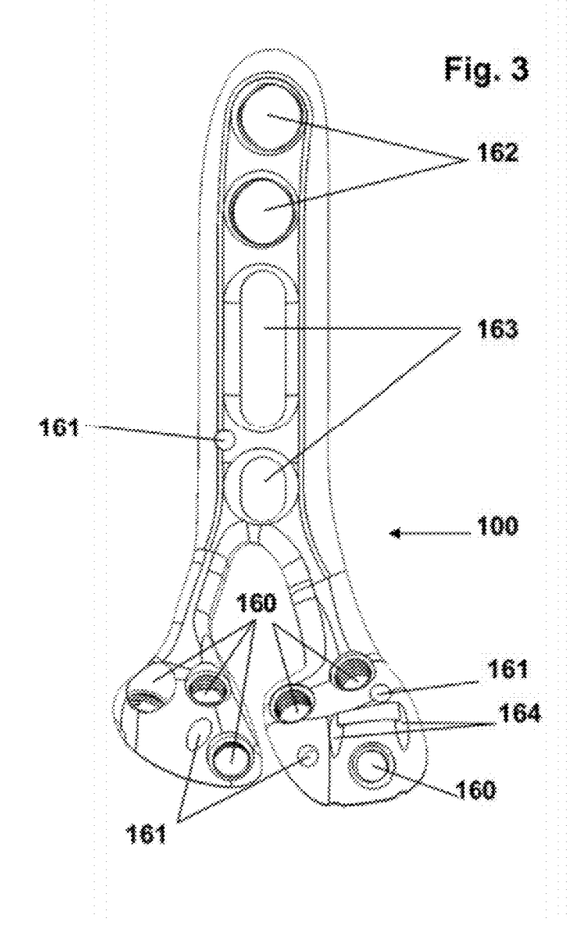
FIG. 3 is an additional top view of the fracture fixation plate of FIG. 1 showing additional features of the present invention.
Figure 4:
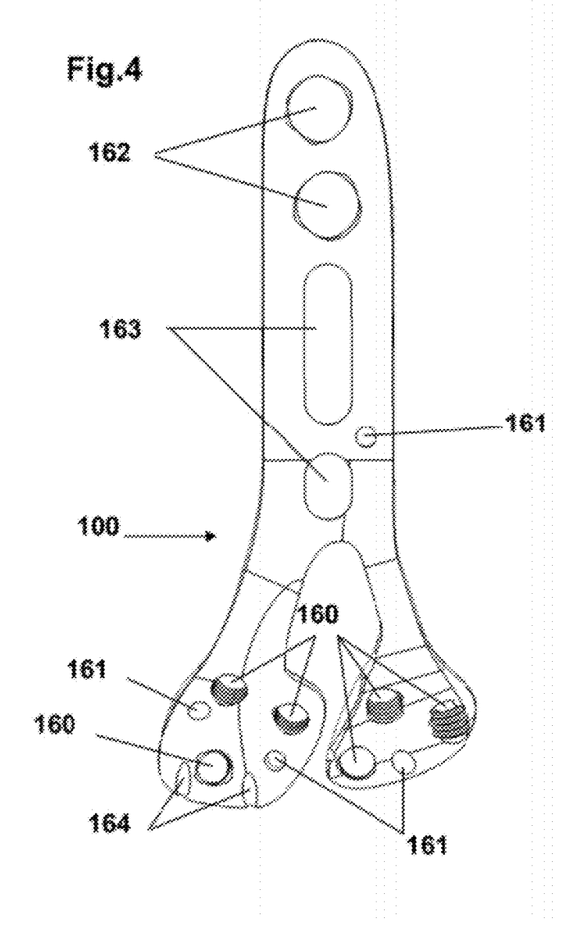
FIG. 4 is an additional bottom view of the fracture fixation plate of FIG. 2 showing additional features of the present invention.

Referring to FIGS. 1 and 2, a generally "Y" shaped fracture fixation plate 100 is shown having a bone contacting surface 101 and an opposite surface 102, a straight or slightly curving elongated body portion 110 having a proximal end and a distal end and a plurality of independently adjustable head portions 120, 130. The plurality of head portions are angled relative to the body portion 110 about ulnar lateral axis u1 and radial lateral axis, r1 that diverge distally. In one embodiment of the present invention, for use as a volar radius fixation plate, the plurality of head portions are embodied as an ulnar head portion 120 and a radial head portion 130. Head portions 120 and 130 are independently connected to body portion 110, respectively, by ulnar neck portion 125 and radial neck portion 135 which branch out angularly from the distal end of body portion 110 and are independently adjustable. Body portion 110 is intended to be anchored to the diaphysis portion of a bone while ulnar and radial head portions 120 and 130 are adapted to anchor, respectively, the ulnar and radial metaphyseal fragments of a fracture. The gap 140 formed between head portions 120 and 130 as well as between neck portions 125 and 135 allows for good visualization of the fracture line.

Referring now to FIGS. 1-4 radial head portion 130 of fracture fixation plate 100 includes a plurality of threaded holes 160. In this particular embodiment, the radial head portion 130 includes three threaded holes 160. The threaded holes 160 are arranged non-linearly, e.g.: as vertices of a triangle if three holes 160 are present. In alternate embodiments, if more than three threaded holes 160 are present, the holes are arranged as vertices of a polygon. Holes 160 are intended to receive bone fasteners (i.e.: screws or pegs, solid or cannulated) having threaded heads that are adapted to engage the threads of holes 160 in either: a.) a fixed angle relationship (i.e.: along the axis of a hole 160) or b.) a variable angle relationship (i.e.: along an axis selected intraoperatively by the surgeon, non-collinear with the axis of a hole 160). Likewise, ulnar head portion 120 includes a plurality of holes of type 160, similarly arranged and having similar functionality to those in radial head portion 130.

Referring again to FIGS. 1-4, radial head portion 130 of fracture fixation plate 100 optionally includes at least one non-threaded hole 161. Holes 161 are intended to receive complimentarily sized Kirschner wires (hereinafter "K-wires") therethrough in a pre-defined angular relationship to the bone contacting surface 101 of head portion 130. The K-wires (shown in FIGS. 9A, 9B and 9C) enter the plate through the opposite surface 102 and exit the fracture fixation plate through the bone contacting surface 101. Likewise, ulnar head portion 120 is optionally provided with at least one hole of type K having identical functionality to those in radial head portion 130 and may optionally be provided with interconnected holes 164 for receiving sutures as will be explained further below.

As further shown in FIGS. 1-4, in the present embodiment, the body portion 110 includes at least one anchoring hole 162, which is threaded and adapted to receive anchoring fasteners with complementarily threaded heads that engage the threads of anchoring holes 162 at a fixed angle relationship (i.e.: collinear to the axes of anchoring holes 162). The axes of threaded holes 162 may optionally be skew (heretofore defined as non-coplanar) relative to each other. Furthermore, the body portion 110 may optionally include one or more non-threaded anchoring slots 163, for receiving compression screws permitting the temporary repositioning of the plate relative to the underlying bone during surgery. Body portion 110 may optionally include one or more holes K intended to receive complimentarily sized K-wires for temporary anchoring of the body portion to the bone.

Figure 5:
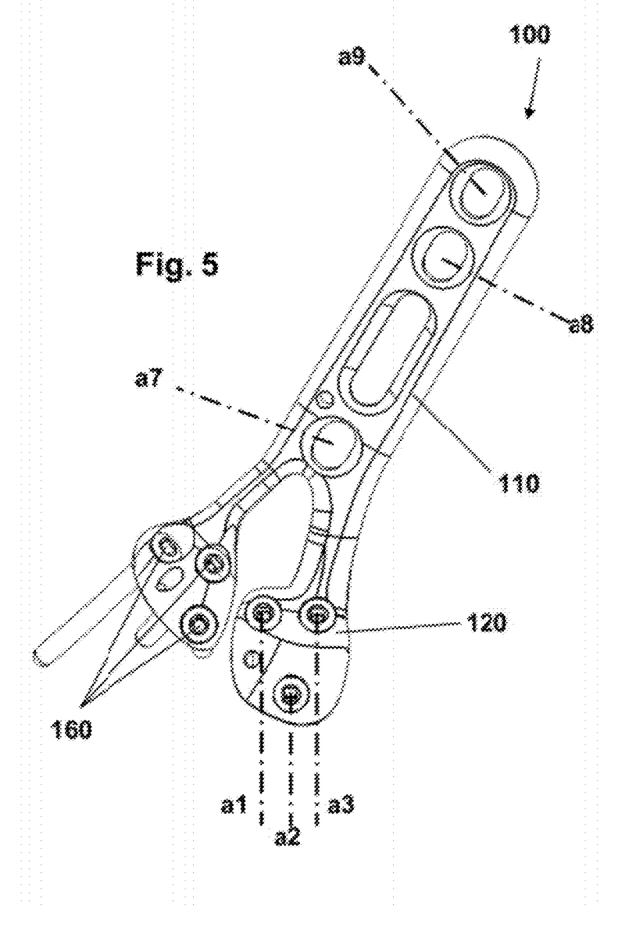
FIG. 5 is a top orthogonal view of a fracture fixation plate in accordance with the present invention illustrating the skew axes defined by holes in the ulnar head portion of the fracture fixation plate.
Figure 6:
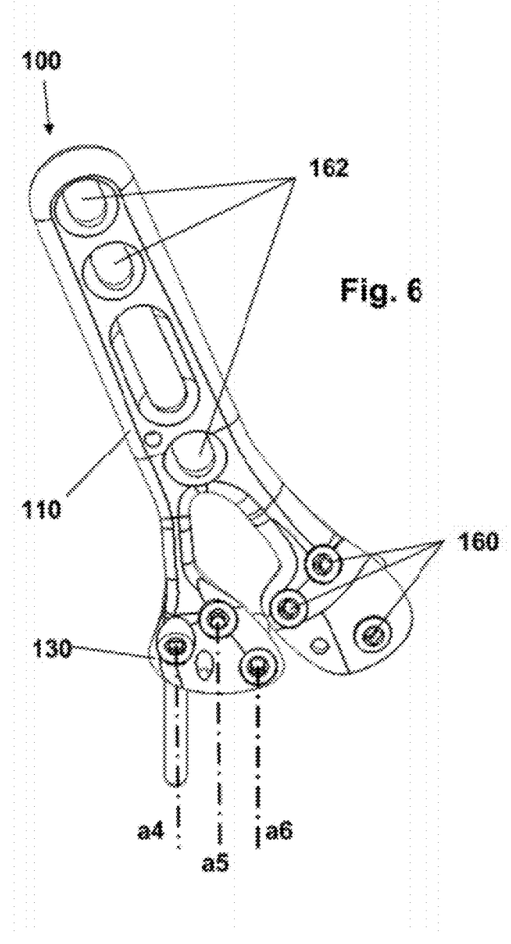
FIG. 6 is top orthogonal view of a fracture fixation plate in accordance with the present invention illustrating the skew axes defined by holes in the radial head portion of the fracture fixation plate.

Referring now to FIGS. 5-6, therein is shown one embodiment of a fracture fixation plate 100 having axes a1 through a9 defined by the plurality of holes 160 and 162. The actual number of axes a1, a2 . . . aN in a particular fracture fixation plate is a function of the number of holes 160 and 162 existing in that particular embodiment of the fracture fixation plate. Axes a1, a2 and a3 in ulnar head portion 120 are skew (non-coplanar, as previously defined) relative to each other but exist in planes that are mutually parallel. Axes a4, a5, and a6 in radial head portion 130 are also skew relative to each other and also exist in planes that are mutually parallel. However, the parallel planes where the first set of axes (a1, a2, a3) exist are not parallel to the parallel planes where the second set of axes (a4, a5, a6) exist but, instead, the first set of parallel planes diverges distally relative to the second set of parallel planes. This arrangement is advantageous because skew lines are inherent to the formation of surfaces that mimic the shape of the articular surface of at least one bone in a joint. Axes a7, a8 and a9 in body portion 110 may optionally be skew relative to each other. This is also advantageous since fasteners anchored along skew axes provide better anchorage of the plate to the diaphysis of osteoporotic bone than equivalent fasteners with parallel axes.

Figure 7:
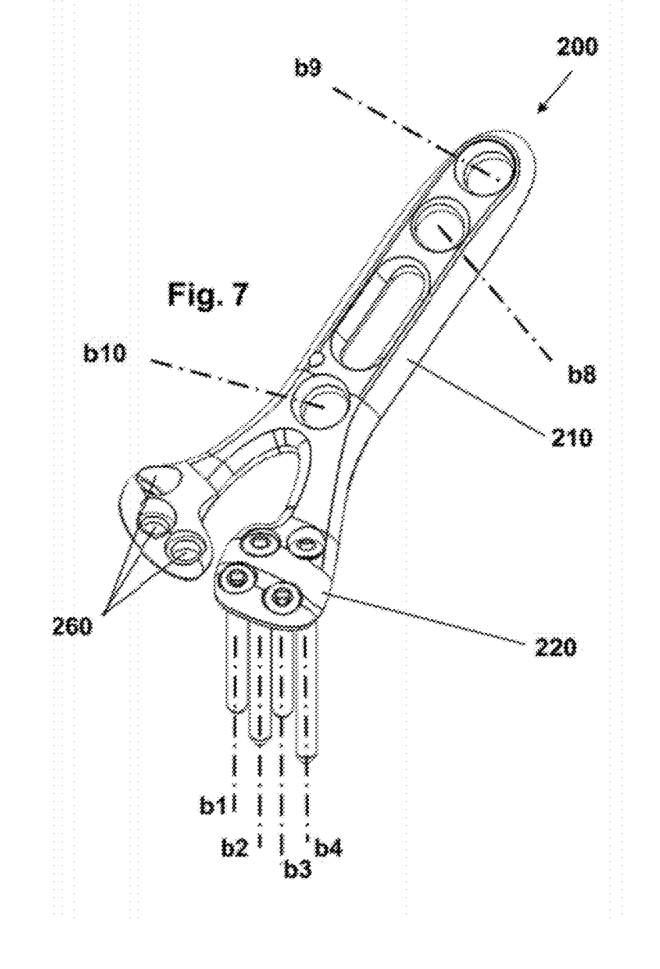
FIG. 7 is a top orthogonal view of an alternate embodiment of a fracture fixation plate in accordance with the present invention illustrating the skew axes defined by holes in the ulnar head portion of the fracture fixation plate.
Figure 8:
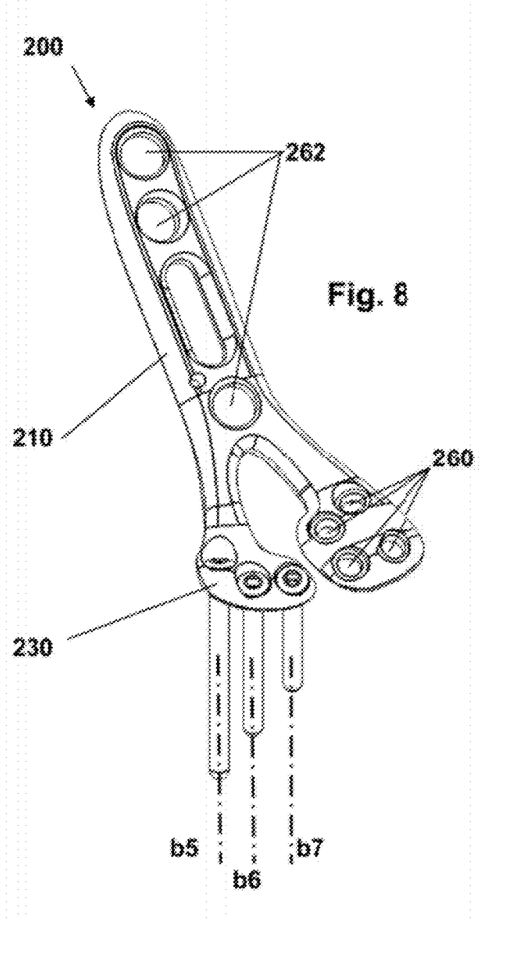
FIG. 8 is top orthogonal view of an alternate embodiment of a fracture fixation plate in accordance with the present invention illustrating the skew axes defined by holes in the radial head portion of the fracture fixation plate.

Referring now to FIGS. 7-8, therein is shown an alternate embodiment of a fracture fixation plate 200 having axes b1 through b10 defined by the plurality of threaded holes 260 and 262. In this particular embodiment the ulnar head portion 220 defines four threaded holes 260 arranged as vertices of a four-sided polygon. Axes b1, b2, b3 and b4 of the threaded holes 260 in ulnar head portion 220 are skew relative to each other but exist in planes that are parallel. Axes b5, b6 and b7 of the threaded holes 260 in radial head portion 230 are also skew relative to each other and also exist in planes that are parallel. As in the case of fracture fixation plate 100, the parallel planes where the first set of axes (b1, b2, b3 and b4) exist are not parallel to the parallel planes where the second set of axes (b5, b6 and b7) exist but, instead, the first set of parallel planes diverges distally relative to the second set. Axes b8, b9 and b10 of threaded holes 262 in body portion 210 are also skew relative to each other.

Figure 9A:
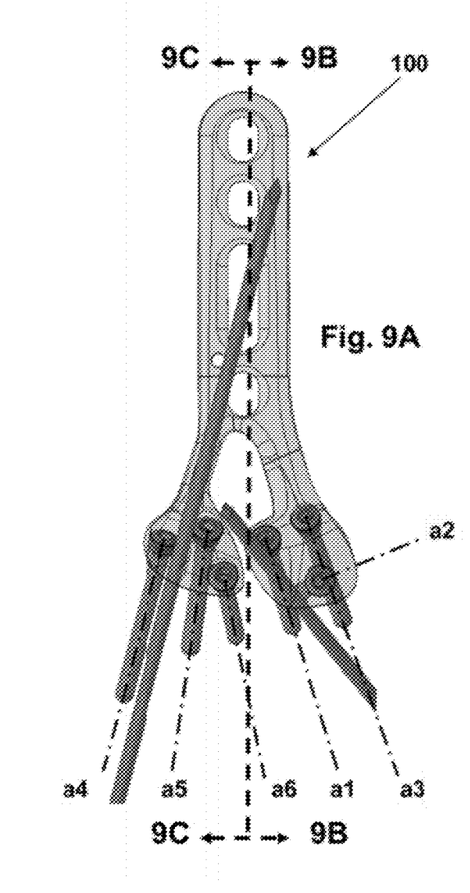
FIG. 9A is a top view (semi-transparent for clarity) of a fracture fixation plate in accordance with the present invention with bone fasteners and K-wires installed therein.
Figure 9B:
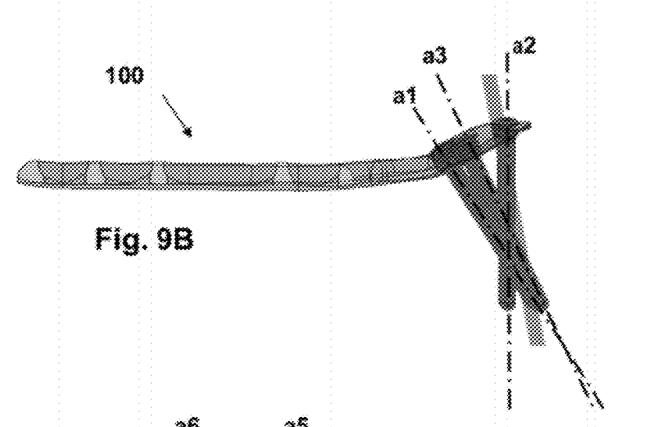
FIG. 9B is a longitudinal cross section of the fracture fixation plate in FIG. 9A showing the ulnar side of the fracture fixation plate.
Figure 9C:
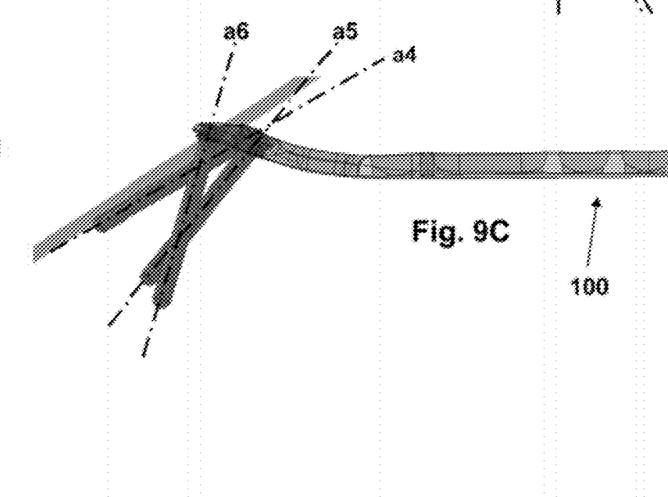
FIG. 9C is a longitudinal cross section of the fracture fixation plate in FIG. 9A showing the radial side of the fracture fixation plate.

Referring now to FIG. 9A, therein is shown a plan view of fracture fixation plate 100 (transparent, for clarity) indicating the alignment of axes a1, a2, a3, a4, a5 and a6 of ulnar head 120 and radial head 130 in an example of one embodiment of the present invention. FIGS. 9B and 9C, respectively, show longitudinal cross sections of fracture fixation plate 100. FIG. 9B shows the ulnar side cross section view of the alignment of axes a1, a2 and a3 of the ulnar head 120. FIG. 9C shows the radial side cross section view of the alignment of axes a4, a5 and a6 on radial head 130.

Figures 10A, 10B, 10C:
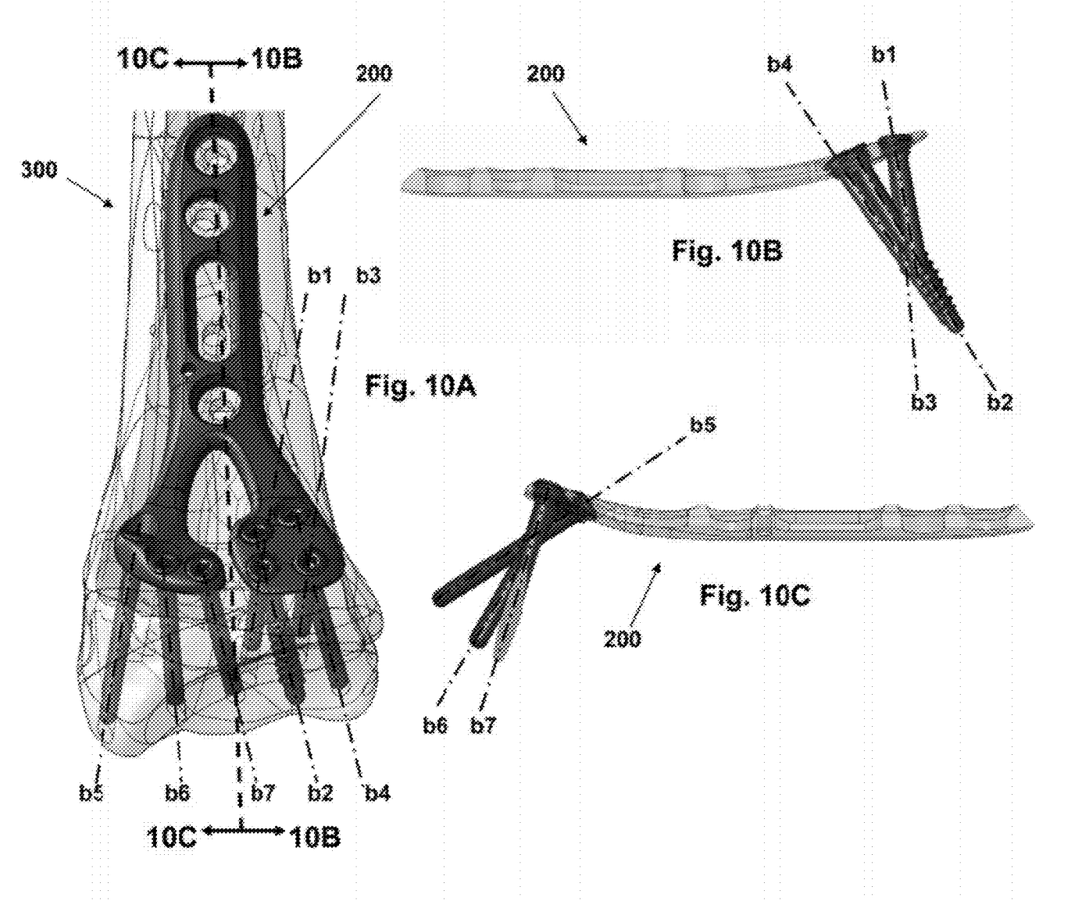
FIG. 10A is a top view of a fracture fixation plate in accordance with an alternate embodiment of the present invention with bone fasteners installed therein, and superimposed on a human radius bone to illustrate its relative positioning.
FIG. 10B is a longitudinal cross section of the fracture fixation plate in FIG. 10A showing the ulnar side of the fracture fixation plate.
FIG. 10C is a longitudinal cross section of the fracture fixation plate in FIG. 10A showing the radial side of the fracture fixation plate.

Referring now to FIG. 10A therein is shown a perspective view of the distal volar side of a radius bone 300, transparent for clarity, with an alternate embodiment 200 of the fracture fixation plate of the instant invention superimposed in the correct position on the bone 300 and indicating the alignment of axes b1, b2, b3 and b4 of the threaded holes and the corresponding fasteners of the ulnar head portion 220 and axes b5, b6 and b7 of the threaded holes and the corresponding fasteners of the radial head portion 230. FIGS. 10B and 10C are, respectively, longitudinal cross sections of fracture fixation plate 200. FIG. 10B shows the alignment of axes b1, b2, b3 and b4 of the threaded holes and the corresponding fasteners of ulnar head portion 220. FIG. 10C shows the alignment of axes b5, b6 and b7 of the threaded holes and the corresponding fasteners of radial head portion 230. The alignment of the axes of threaded holes 260 on each of the head portions and, correspondingly, the axes of the bone fasteners installed thereupon, are skew relative to each other to advantageously provide subchondral support of the articular surface at the lunate fossa and scaphoid fossa.

Figure 11:
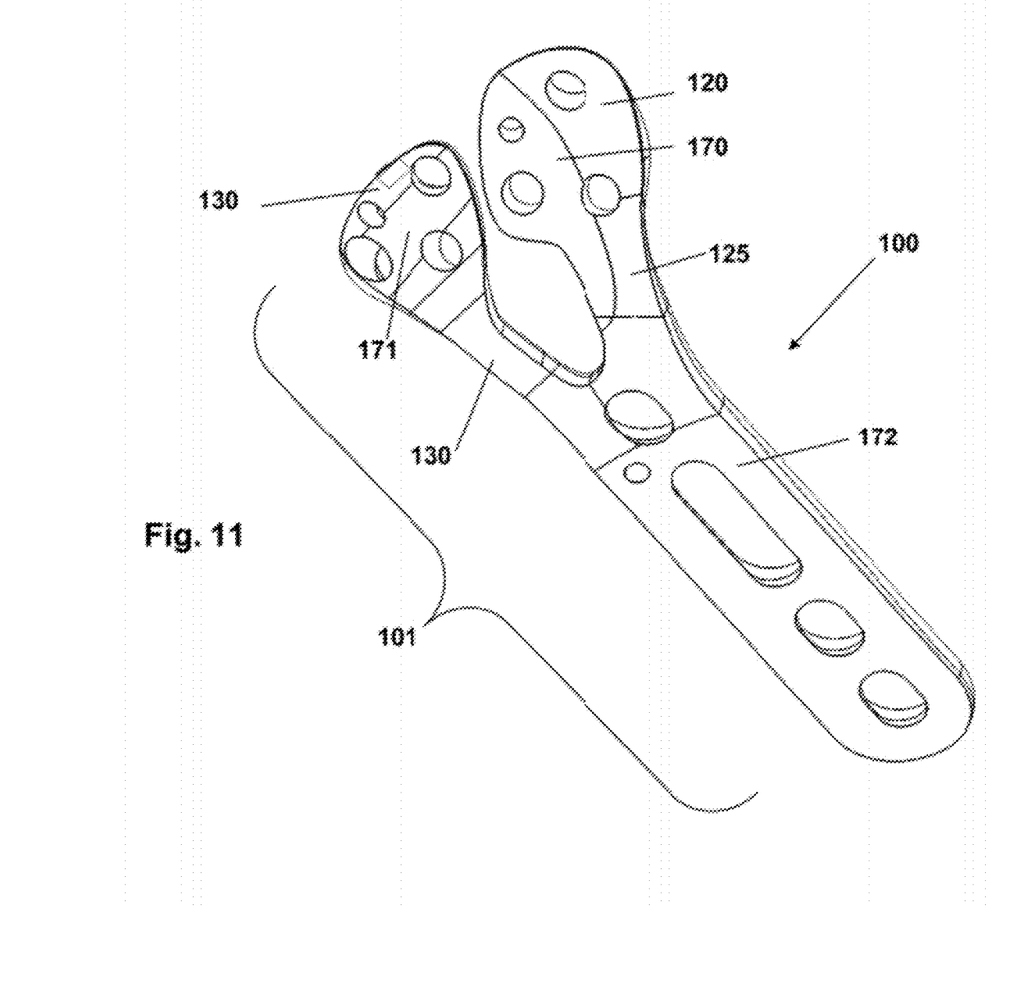
FIG. 11 is a bottom orthogonal view of a fracture fixation plate in accordance with the present invention illustrating various portions of the bone contacting surface of the fracture fixation plate.

Referring now to FIG. 11 therein is shown a perspective view of particular portions of the bone contacting surface 101 of one embodiment 100 of the fracture fixation plate of the instant invention. In the ulnar head portion 120 the bone contacting surface 170 is spherically concave. In the radial head portion 130 the bone contacting surface 171 is substantially flat. In the body portion 110 the bone contacting surface 172 is cylindrically concave in relation to the longitudinal axis of the body portion 110. Alternate fracture fixation plate embodiments optionally may include similar geometrical characteristics of the corresponding surfaces.

Figure 12:
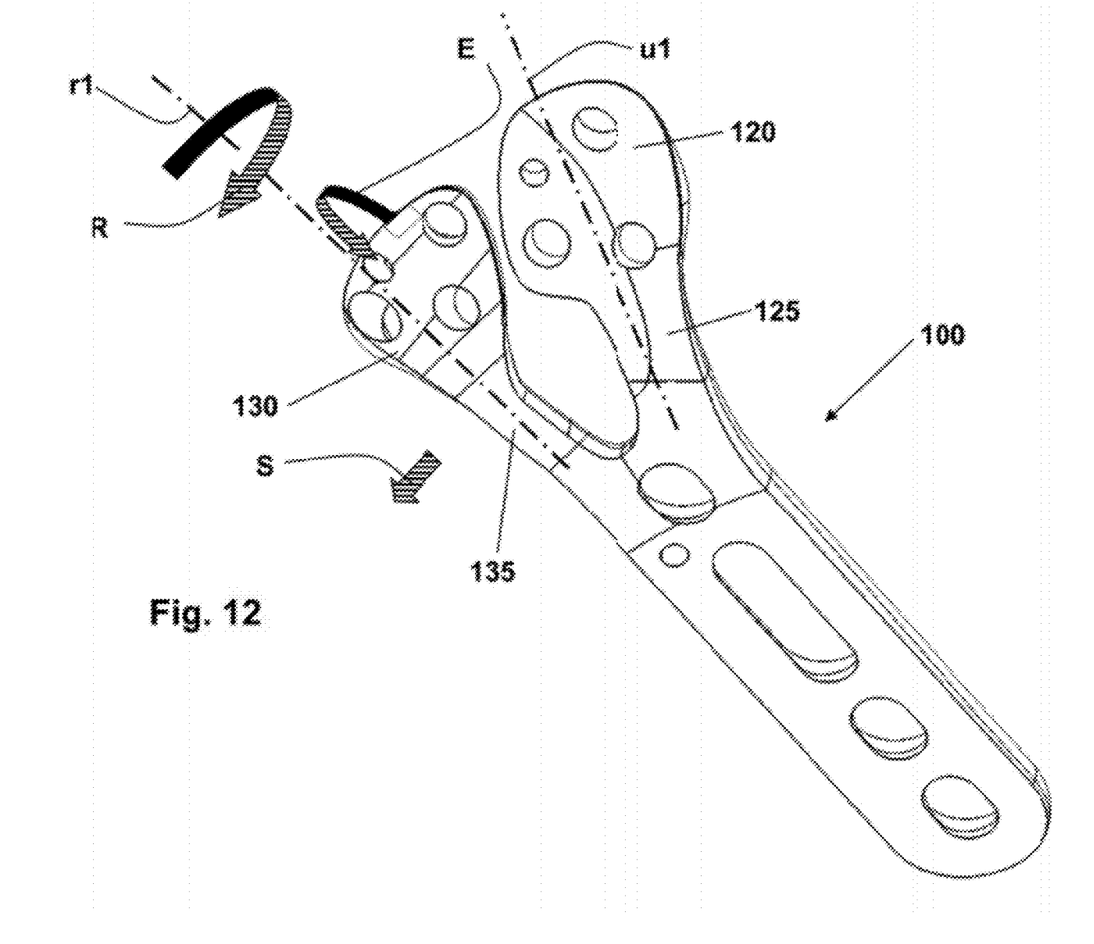
FIG. 12 is a bottom orthogonal view of a fracture fixation plate in accordance with the present invention illustrating the range of adjustability of the position of the radial head portion of the fracture fixation plate.

Referring now to FIG. 12, therein is indicated the range of adjustability of the position of radial head portion 130 of fracture fixation plate 100: 1.) separation S between head portions 130 and 120; 2.) elevation E of the head portion 130 relative to the bone surface and 3.) rotation R of the head portion 130 around the longitudinal axis r1 of radial neck portion 135. The range of adjustability is illustrated by way of example and is not intended to be limiting. The adjustments may be accomplished by the use of plate bending tools to apply appropriate bending and/or torqueing force to radial neck portion 135. The adjustments are advantageous because they facilitate achieving the best contact possible between the bone contacting surfaces of the plate 100 and the underlying bone and bone fragments. Although indicated in FIG. 12 as referring to radial head portion 130, similar positional adjustment can be accomplished on ulnar head portion 120. Alternate embodiments of the fracture fixation plate optionally may include similar positional adjustment features.

Figure 13:
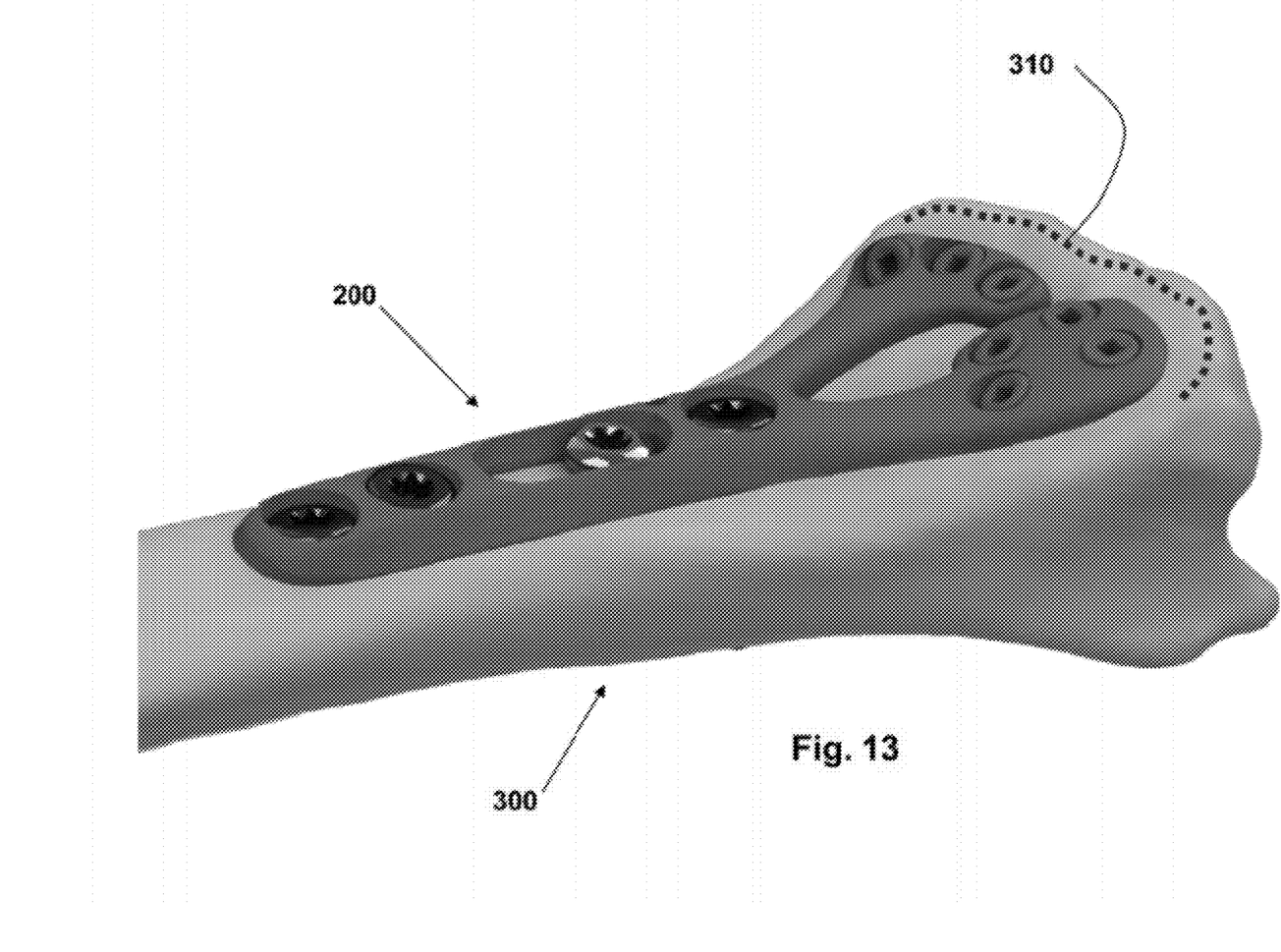
FIG. 13 is a perspective view of an alternate embodiment of a fracture fixation plate in accordance with the present invention installed on a human radius bone illustrating its position relative to the watershed line.
Figure 14A:
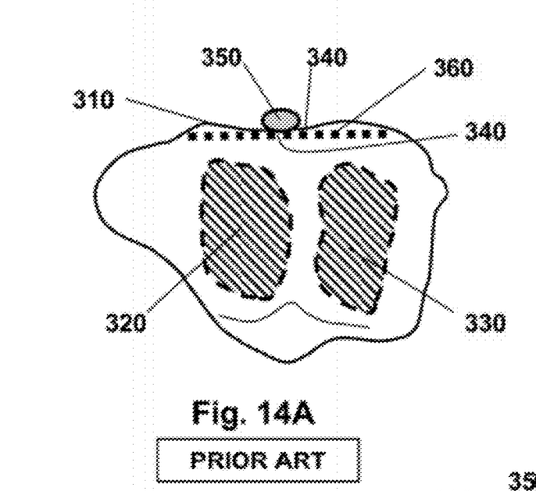
FIGS. 14A and 14B are diagrams illustrating the relative positioning between a flexor tendon in the volar side of the human radius bone and prior art single-headed fracture fixation plates.
Figure 14B:
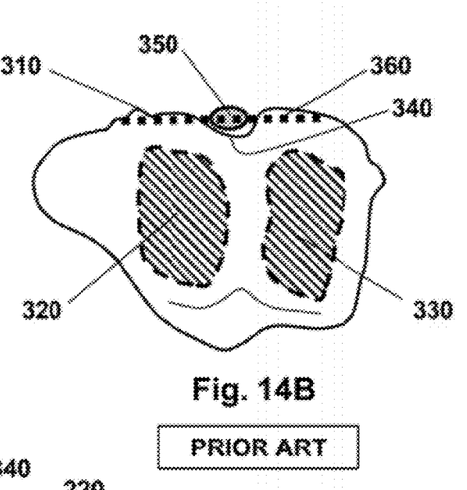
Figure 14C:
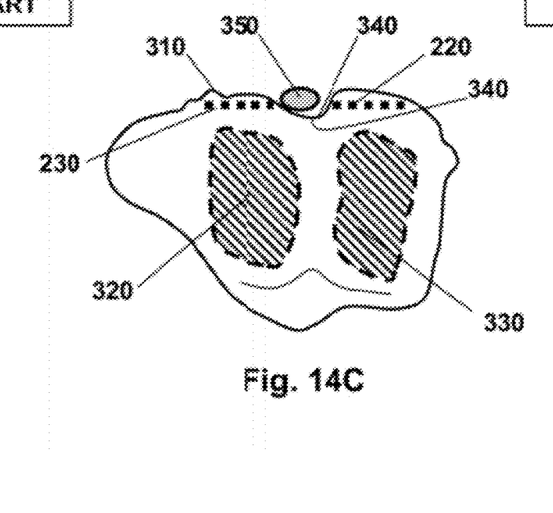
FIG. 14C is a diagram illustrating the relative positioning between a flexor tendon in the volar side of the human radius bone and a fracture fixation plate in accordance with the present invention.

As previously described above, the instant invention provides a fracture fixation plate with a plurality of head portions. This is particularly advantageous for minimizing the risk of post-operative flexor tendon rupture. Referring to FIG. 13 therein is shown a fracture fixation plate 200 correctly installed on the volar side of a distal radius bone 300 just proximal of the watershed line 310, a theoretical line marking the most volar aspect of the volar margin of the distal radius. Referring now to FIG. 14A therein is shown a diagrammatic view of the articular surface of the distal radius wherein is indicated the scaphoid fossa 320, the lunate fossa 330 and the inter-fossae sulcus 340 and the edge of the watershed line 310. Also shown diagrammatically is a flexor tendon 350 (for example: the Flexor Pollicis Longus). In some patients, the inter-fossae sulcus 340 is relatively shallow at the watershed line 310 and this allows for the correct installation of a single headed fracture fixation plate 360 (shown dotted) just beyond of the watershed line 310 without post-operative impingement with a flexor tendon 350. However, as shown in FIG. 14B, in other patients, the inter-fossae sulcus 340 is much deeper at the watershed line 310. The installation of a single headed plate (shown dotted), even if correctly installed proximal of the watershed line 310, can lead to post-operative impingement of said plate and a flexor tendon 350 resulting in tenosynovitis or rupture of the tendon. Referring now to FIG. 14C therein is shown, diagrammatically in dotted line, the installed position of a double headed fracture fixation plate of the instant invention wherein the gap between the radial head portion 230 and the ulnar head portion 220 of the plate allows for the movement of the flexor tendon 350 free of impingement with either of said heads.

Figure 15A:
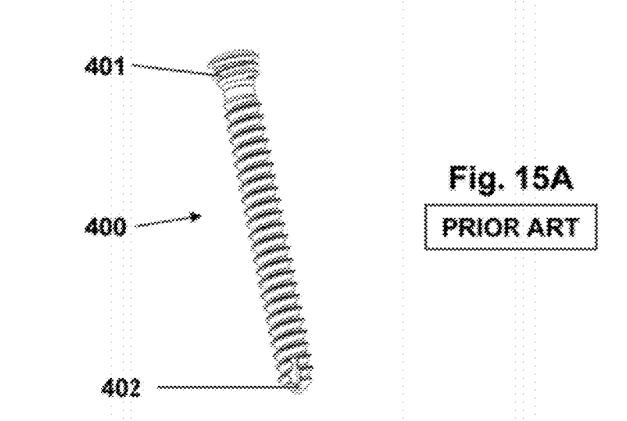
FIGS. 15A and 15B show, respectively, prior art threaded fastener and the relative positioning between an extensor tendon and the prior art threaded fastener affixed to a fracture fixation plate installed on the human radius bone.
Figure 15B:
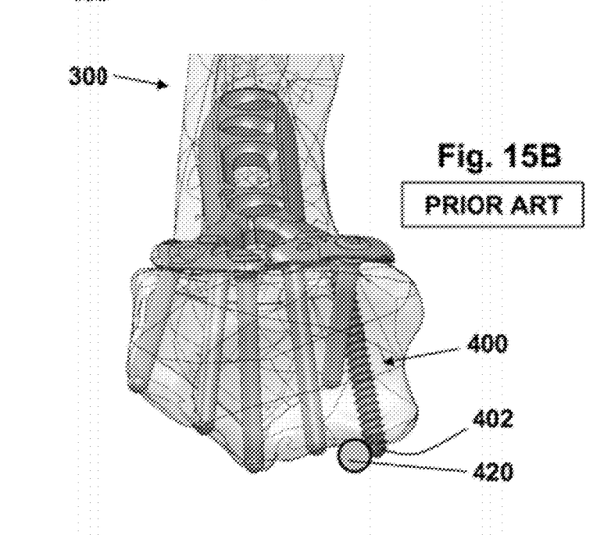
Figure 15C:
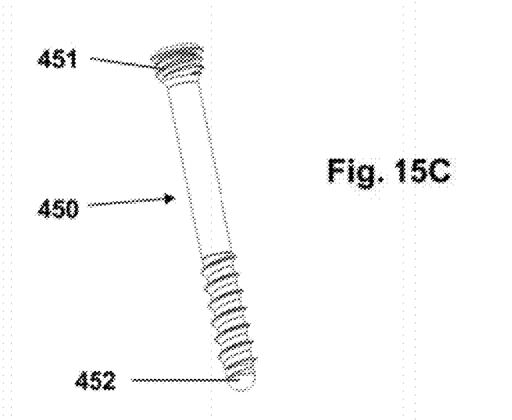
FIGS. 15C and 15D show, respectively, a threaded fastener in accordance with the present invention and the relative positioning between an extensor tendon and a threaded fastener in accordance with the present invention affixed to a fracture fixation plate installed on the human radius bone.
Figure 15D:
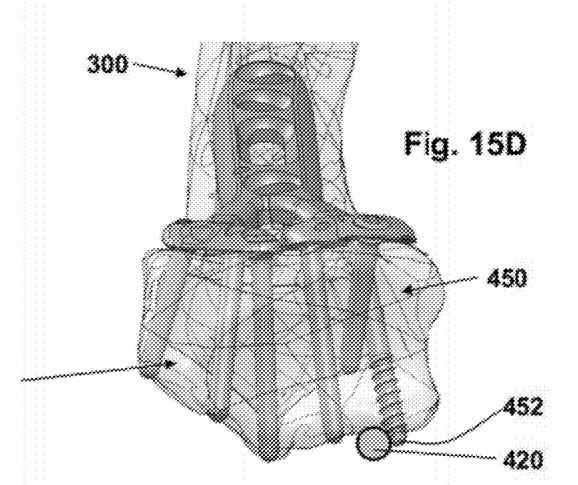

In a further advantageous aspect of the instant invention, a threaded fastener is provided for the purpose of minimizing the risk of post-surgical extensor tendon rupture. Referring now to FIGS. 15A-15D and in particular, FIG. 15A therein is shown a prior art threaded fastener 400 having a threaded head 401 for engaging a threaded hole 160 of fracture fixation plate 100 and an opposite bone engaging threaded sharp end 402. If, as can frequently occur and shown in FIG. 15B, the sharp end 402 of the threaded fastener 400 should protrude even minimally through the dorsal aspect of a distal radius bone 300, the sharp end 402 can injure, and even cause rupture, of extensor tendon 420. As shown in FIG. 15C the instant invention provides a threaded fastener 450 having a threaded head 451 for engaging a threaded hole 160 of fracture fixation plate 100 and an opposite, bone engaging, rounded end 452 that is atraumatic. As shown in FIG. 15D, should the threaded fastener 450 protrude as much as 2 mm through the dorsal aspect of the radius, the rounded end 452 of the fastener will not injure or rupture the extensor tendon 420.

As previously discussed, threaded holes 160, 260 of fracture fixation plates 100, 200 are intended to receive fasteners (i.e.: solid pegs or screws) with threaded heads adapted to engage the threads in holes 160, 260. These fasteners can be received at fixed angles, that is, collinearly with the axes of the corresponding hole 160, 260. However, it is one object of the instant invention to provide improved targeting and fixing of particular fractured bone fragments and in many instances this is difficult to accomplish by fixed angle fasteners. Accordingly, to accomplish this purpose, alternative embodiments of the present invention may employ cannulated, variable angle fasteners.

Figures 16A, 16B:
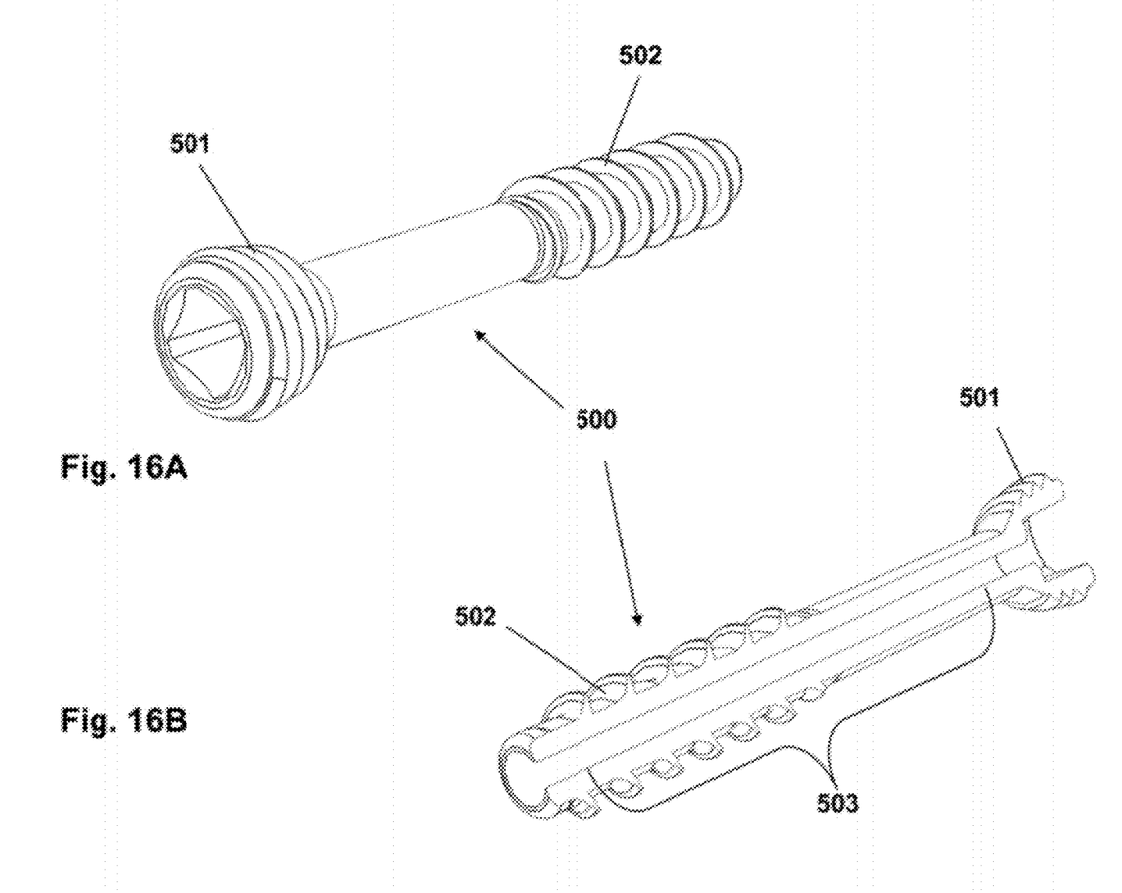
FIG. 16A is a perspective view of a variable angle cannulated fastener in accordance with the present invention
FIG. 16B is a longitudinal, perspective cross-section view of variable angle cannulated fastener in accordance with the present invention.

Referring now to FIGS. 16A-16B therein is shown one embodiment of a cannulated variable angle fastener 500 adaptable for use with the present invention. FIG. 16A shows a perspective of a variable angle cannulated fastener 500, in this instance a screw, having a tapered threaded head 501 adapted to engage a threaded hole 160, 260 at an angle selected by the surgeon. Variable angle cannulated fastener 500 may optionally have a threaded portion 502 adapted to engaging a bone fragment.

FIG. 16B shows a longitudinal, perspective cross-section of variable angle fastener 500 with longitudinal cannula 503 extending through the entire length of variable angle fastener 500 and open at both ends. The cannula 503 of variable angle fastener 500 is adapted to be inserted over an appropriately sized K-wire.

Bone fragments to be fixated using the fracture fixation plate 100, 200 of the present invention may be targeted by the surgeon under fluoroscopy. A K-wire is inserted through a selected threaded hole 160, 260 and drilled into an identified bone fragment, which is then over-drilled with a cannulated drill or hole saw. The drill is removed and the cannulated fastener, 500 is inserted over the K wire to engage the bone fragment. Since the axis of the drilled K-wire is likely to be non-collinear with the axis of threaded hole 160 the thread 501 of the head portion of cannulated variable angle fastener 500 must be able to cross-thread into the thread of threaded hole 160, 260. To accomplish this, fastener 500 must be made of harder material than the head portions 120, 130, 220, 230 of the fracture fixation plate 100, 200. For example, fastener 500 may be made of cobalt chromium while the fracture fixation plate 100, 200 is made of titanium.

Figure 17:
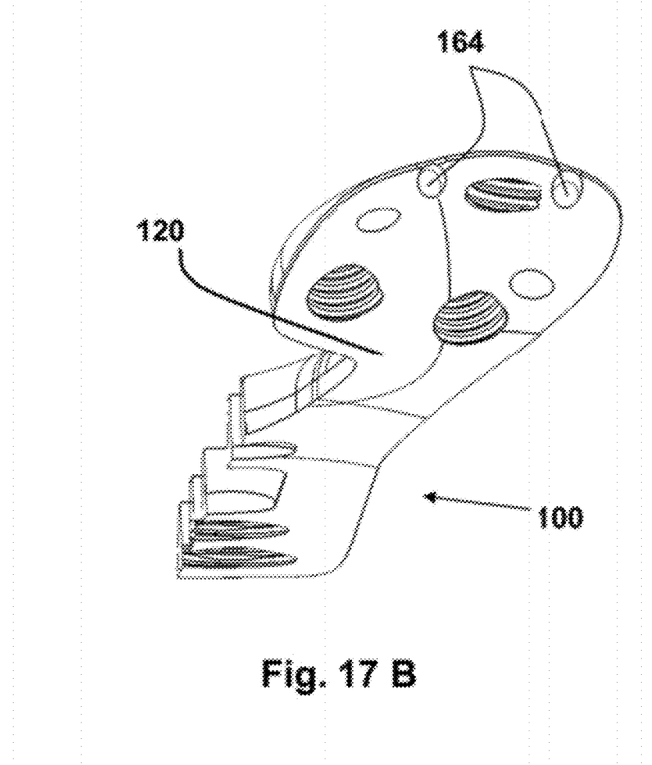
FIG. 17A is a partial top orthogonal view of an alternate embodiment of a fracture fixation plate in accordance with the present invention illustrating suture holes and a communicating channel therebetween.
FIG. 17B is a bottom orthogonal view of the fracture fixation plate in FIG. 16A.

As previously indicated above, ulnar head portion 120 of fracture fixation plate 100 may optionally include suture holes 164. Suture holes 164 are non-threaded and mutually communicating and are intended to receive sutures for tension binding small volar marginal fragments of bone. FIGS. 17A and 17B show in greater detail suture holes 164 in ulnar head portion 120 and their communicating channel 165 adapted to accommodate the suture knot. If desired suture holes 164 may optionally be provided in radial head portion 130 (not shown). Similar suture holes 164 may optionally be provided in alternate embodiments; for example 200, of the fracture fixation plate of the instant invention.

Although described above in connection with a volar fracture fixation plate and system for the distal radius, these descriptions are not intended to be limiting, as other plates can be made in accordance with the description herein, but of different size or scale, so as to treat other fractures, as desired. As such, although the invention is illustrated and described herein, various modifications and structural changes may be made therein without departing from the spirit of the invention and within the scope and range of equivalents of the claims.

We claim:

1. A fracture fixation plate for application to the volar surface of the distal radius, said plate comprising:
   a substantially rigid plate including an elongated body portion having proximal and distal ends and defining a longitudinal body axis;
   said plate including a bone contacting surface and an opposite surface
   said plate including an ulnar head portion and a radial head portion, each of said head portions independently connected to the distal end of said body portion by a corresponding neck portion;
   each of said neck portions being narrower than the widest part of its corresponding head portion;
   each of said neck portions disposed about a neck axis therethrough, extending distally from said distal end of said body portion to its corresponding head portion;
   each of said head portions including a plurality of threaded holes adapted to receive bone fasteners;
   each of said threaded holes defining a bone fastener axis;
   said body portion including at least one anchoring hole;
   wherein each of said neck axes corresponding to each said neck portions diverges distally from each adjacent neck axis defining an angle therebetween;
   wherein each said angle defined between each of said neck axes and any other adjacent neck axis is an acute angle;
   wherein said ulnar head portion is substantially square-shaped and said bone contacting surface of said ulnar head portion is spherically concave to conform to the ulnar metaphyseal surface of the volar aspect of a distal radius bone;
   wherein said radial head portion is substantially triangle-shaped and said bone contacting surface of said radial head portion is flat to conform to the radial metaphyseal surface of the volar aspect of a distal radius bone, and
   wherein said ulnar head portion and said radial head portion, in combination, are adapted to substantially cover the volar surface proximal to the watershed line of the distal radius bone.

2. The fracture fixation plate of claim 1 wherein said head portions, neck portions and body portion are arranged to comprise a generally "Y" shaped plate.

3. The fracture fixation plate of claim 2 wherein said two neck portions and two head portions define a gap therebetween adapted to facilitate visualization of a fracture line and accommodate a tendon to avoid impingement thereof.

4. The fracture fixation plate of claim 1 wherein said bone contacting surface of said body portion is longitudinally cylindrically concave.

5. The fracture fixation plate of claim 1 wherein one or more of said ulnar head portion and said radial head portion is independently adjustable relative to said body portion through deformation of the neck portion corresponding to said head portion.

6. The fracture fixation plate of claim 1 wherein at least one of said anchoring holes is threaded and defines an anchoring fastener axis.

7. The fracture fixation plate of claim 1 further comprising one or more holes adapted to receive a K-wire.

8. The fracture fixation plate of claim 7 wherein at east one of said holes adapted to receive a K-wire is located in at least one of said head portions.

9. The fracture fixation plate of claim 1 further comprising a plurality of suture holes on one or more of said head portions.

10. The fracture fixation plate of claim 9 wherein at least two of said plurality of suture holes communicate through a suture hole communicating channel extending between said suture holes on said opposite surface.

* * * * *